US012797310B2

(12) United States Patent
Meunier et al.

(10) Patent No.: US 12,797,310 B2
(45) Date of Patent: Nov. 17, 2026

(54) COMPOSITION COMPRISING HECTORITE AND PECTIN

(71) Applicant: L'OREAL, Paris (FR)

(72) Inventors: Christine Meunier, Chevilly Larue (FR); Olga Biganska, Chevilly Larue (FR); Franck Clement, Saint-Ouen (FR)

(73) Assignee: L'OREAL, Paris (FR)

( * ) Notice: Subject to any disclaimer, the term of this patent is extended or adjusted under 35 U.S.C. 154(b) by 603 days.

(21) Appl. No.: 17/297,765

(22) PCT Filed: Nov. 28, 2019

(86) PCT No.: PCT/EP2019/082961

§ 371 (c)(1),
(2) Date: May 27, 2021

(87) PCT Pub. No.: WO2020/109500

PCT Pub. Date: Jun. 4, 2020

(65) Prior Publication Data

US 2022/0110839 A1 Apr. 14, 2022

(30) Foreign Application Priority Data

Nov. 29, 2018 (FR) ....................................... 1872066

(51) Int. Cl.
*A61K 8/25* (2006.01)
*A61K 8/04* (2006.01)
*A61K 8/06* (2006.01)
*A61K 8/73* (2006.01)

(52) U.S. Cl.
CPC .............. *A61K 8/042* (2013.01); *A61K 8/062* (2013.01); *A61K 8/25* (2013.01); *A61K 8/732* (2013.01)

(58) Field of Classification Search
CPC .......... A61K 8/042; A61K 8/062; A61K 8/25; A61K 8/732; A61K 8/26; A61K 8/73; A61Q 5/02; A61Q 19/00
See application file for complete search history.

(56) References Cited

U.S. PATENT DOCUMENTS

| | | | | |
|---|---|---|---|---|
| 2006/0013790 A1* | 1/2006 | Shimizu | A61Q 19/00 | 424/70.12 |
| 2008/0226756 A1* | 9/2008 | Willemin | A61Q 19/08 | 424/769 |
| 2010/0112017 A1* | 5/2010 | Mizutani | A61Q 19/10 | 424/78.03 |
| 2016/0008236 A1* | 1/2016 | Valverde | A61K 8/042 | 514/777 |

FOREIGN PATENT DOCUMENTS

| | | |
|---|---|---|
| CN | 105342873 A | 2/2016 |
| FR | 2 292 027 | 6/1976 |
| WO | WO 97/17944 A1 | 5/1997 |

OTHER PUBLICATIONS

INCIDecoder. (Aug. 12, 2017). Sucrose. https://web.archive.org/web/20170812143329/https://incidecoder.com/ingredients/sucrose (Year: 2017).*
Patel et al. Natural and synthetic layered materials as cosmetic ingredients, Household and Personal Care Today, 4:31-26, 2010 ( Year: 2010).*
International Search Report issued on Feb. 27, 2020 in PCT/EP2019/082961 filed on Nov. 28, 2019, 3 pages.
French Preliminary Search Report (with English translation of Categories of Cited Documents) issued on Jul. 19, 2019 in French Application 1872066 filed on Nov. 29, 2018, 3 pages.

* cited by examiner

*Primary Examiner* — Sahana S Kaup
*Assistant Examiner* — Ashlee E Wertz
(74) *Attorney, Agent, or Firm* — Oblon, McClelland, Maier & Neustadt, L.L.P.

(57) ABSTRACT

The present invention relates to a gel-type composition, preferably a cosmetic composition, comprising at least one pectin and an unmodified hectorite. The invention also relates to a cosmetic process comprising at least one step that consists in applying a composition as defined above to the skin and/or the hair.

18 Claims, No Drawings

COMPOSITION COMPRISING HECTORITE AND PECTIN

The present invention relates to a composition for topical application, comprising pectin and unmodified hectorite, and to the use of said composition notably in the cosmetic field and in particular for caring for, cleansing, protecting and/or making up keratin materials such as the skin, notably bodily or facial skin, or the hair, preferably for caring for bodily or facial skin.

The present invention relates in particular to the field of cosmetic compositions for caring for keratin materials, and notably the skin.

TECHNICAL FIELD

There is at the current time increasing consumer demand for cosmetic or nutritional products which are termed "natural" because they use, as essential components, ingredients that are natural, of natural origin and/or certified organic.

Thus, natural products occupy an increasingly important place in the field of skincare and haircare products.

However, the performance of natural products is often considered by consumers to be inferior to that of conventional products.

In addition, today's society and consumers are also in search of products whose manufacture gives rise to the smallest possible environmental impact.

In this context, formulators are faced with a technical challenge, since they cannot use conventional synthetic starting materials such as efficient non-soaping emulsifiers, thickeners such as crosslinked or non-crosslinked polyacrylic polymers, or silicones.

Thus, it remains difficult to manufacture natural cosmetic products, which have the least possible environmental impact, which are stable and which have sensory performance qualities equivalent or superior to those of conventional products and particular cosmetic performance qualities, notably in terms of a fresh effect, an antipollution effect, visibility of the pores, no tackiness, no running, no soaping, or in terms of provision of a matt effect.

Furthermore, compositions which have a pH as close as possible to the skin pH are also sought.

PRIOR ART

It is known practice to use clays in cosmetic products. However, these clays are generally either modified clays, not intended to be used in "natural" products, or natural clays, such as kaolin, talc and mica, but which do not have the property of texturizing water.

Natural hectorites moreover exist which can texturize water by means of the presence of interfoliar cations, in order to form aqueous gels. These gels are supports that are very advantageous for manufacturing novel natural cosmetic formulations. However, they are not stable over time and their pH is very basic.

DISCLOSURE OF THE INVENTION

Consequently, users are in search of products which simultaneously meet their expectations in terms of cosmeticity and sensory nature, which have less of an environmental impact, and which preferably favour ingredients that are natural, of natural origin and/or certified organic.

In particular, it would be desirable to have available compositions, preferably cosmetic compositions, based on ingredients that are natural, of natural origin and/or certified organic, which are stable, the pH of which is as close as possible to the skin pH, and which have sensory performance qualities equivalent or superior to those of conventional products and particular cosmetic performance qualities, notably in terms of a fresh effect, an antipollution effect, no tackiness, no running, no soaping, or in terms of provision of a matt effect.

The object of the present invention is, precisely, to meet these needs.

SUMMARY OF THE INVENTION

Thus, according to a first aspect, the present invention relates to a gel-type composition, preferably a cosmetic composition, comprising at least:

one pectin; and one unmodified hectorite.

The inventors have discovered, surprisingly, that the compositions according to the invention are stable and pleasant on application.

In particular, and as illustrated in the examples below, the compositions according to the invention make it possible to obtain a fresh effect and an antipollution effect. The compositions formed have the advantage of not being tacky or runny, they are mild, glidant and fresh on application. Furthermore, they are not soapy, in other words they do not have a white film during application.

Moreover, they have a high level of matt-effect performance.

Finally, their pH is advantageously close to the skin pH.

According to another of its aspects, a subject of the invention is also a cosmetic process comprising at least one step which consists in applying a composition as defined previously to the skin and/or the hair.

Other characteristics, aspects and advantages of the invention will become apparent on reading the detailed description which follows.

DETAILED DESCRIPTION

Pectin

Pectins are linear polymers of α-D-galacturonic acid linked in positions 1 and 4 with a certain proportion of carboxylic groups esterified with a methanol group.

About 20% of the sugars constituting the pectin molecule are neutral sugars (L-rhamnose, D-glucose, D-galactose, L-arabinose, D-xylose).

L-Rhamnose residues are found in all pectins, incorporated into the main chain in positions 1, 2.

Uronic acid molecules bear carboxyl functions. This function gives pectins the capacity for exchanging ions, when they are in $COO^-$ form. Divalent ions (in particular calcium) have the capacity of forming ionic bridges between two carboxyl groups of two different pectin molecules.

In the natural state, a certain proportion of the carboxylic groups are esterified with a methanol group. The natural degree of esterification of a pectin may range between 70% (apple, lemon) and 10% (strawberry) depending on the source used.

Using pectins with a high degree of esterification, it is possible to hydrolyse the $—COOCH_3$ groups so as to obtain weakly esterified pectins. During the de-esterification process, there is no use or introduction of methanol into the product.

Depending on the proportion of methylated or non-methylated monomers, the chain is thus more or less acidic and the gelling functionalities are different.

HM (high-methoxy) pectins are thus defined as having a degree of esterification of greater than 50%, and LM (low-methoxy) pectins are defined as having a degree of esterification of less than 50%.

In the case of amidated pectins, the —$OCH_3$ group is substituted with an —$NH_2$ group.

Pectins are notably sold by the company Cargill under the name Unipectine™ or Unipectine Of 600 C SB, by the company CP-Kelco under the name Genu, and by Danisco under the name Grinsted Pectin.

According to a preferred embodiment, the pectin is chosen from non-methoxy or low-methoxy pectins, and preferably from non-methoxy pectins or pectins comprising a degree of methoxylation of less than 50%.

In particular, the pectin is present in a content ranging from 0.01% to 5% by weight of active material, preferably ranging from 0.1% to 2% by weight of active material and better still ranging from 0.5% to 2% by weight of active material, relative to the total weight of the composition.

According to a particular embodiment, the composition also comprises sucrose, glucose, maltodextrin or a mixture thereof.

According to a preferred embodiment, the composition also comprises sucrose.

According to this embodiment, the pectin is combined with the sucrose and use may advantageously be made of the pectin sold by the company Cargill under the name Unipectine Of 600 C SB (INCI name: pectin (and) sucrose).

Unmodified Hectorite

As indicated previously, a composition according to the invention comprises at least one unmodified hectorite.

In particular, the unmodified hectorite is present in a content of between 0.1% and 10% by weight, notably between 0.5% and 5% by weight, in particular between 1% and 5% by weight, preferably between 2% and 5% by weight or even more preferentially between 0.5% and 5% by weight, relative to the total weight of the composition.

An unmodified hectorite that may notably be used is the product sold by Elementis under the name Bentone EW.

According to a preferred embodiment, in a composition according to the invention, the unmodified hectorite/pectin mass ratio is between 10/1 and 1/10.

In particular, the unmodified hectorite/pectin mass ratio is between 10/1 and 1/2, preferably between 10/1 and 1/1. More particularly, it may be 2/1, 4/1, 4/3 or 1/1.

Surfactant: Betaine

According to an advantageous embodiment, a composition according to the invention also comprises a surfactant chosen from betaines, in particular chosen from ($C_8$-$C_{20}$) alkyl betaines, preferably chosen from cocoyl betaine and cocamidopropyl betaine, and even more preferentially the composition comprises cocoyl betaine.

In particular, the betaines may be present in a content of between 0.15% and 5% by weight of active material, in particular between 0.15% and 3% by weight of active material and preferably between 0.15% and 1% by weight of active material, relative to the total weight of the composition.

Additional Compounds

Polyol

According to a preferred embodiment, the aqueous phase of a composition according to the invention also comprises at least one alcohol, chosen notably from polyols, and in particular chosen from glycols.

Thus, the composition may also comprise a polyol chosen from propylene glycol, 1,3-propanediol, dipropylene glycol, butylene glycol, pentylene glycol, hexylene glycol, caprylyl glycol, glycerol and sugars such as sorbitol, (poly)alkylene glycols, and any mixture thereof.

According to one embodiment, the mass concentrations of polyol range from 0.01% to 70% by weight and preferably from 1% to 40% by weight relative to the total weight of said composition.

Preferably, the mass concentrations of polyol range from 0.1% to 50% by weight and preferably from 5% to 25% by weight relative to the total weight of said composition.

Filler

According to one embodiment, the composition according to the invention may also comprise at least one filler.

According to one variant, the filler is an inorganic (mineral) filler.

According to one variant, the filler is an organic filler.

According to one variant, the fillers present in the composition are a mixture of at least one inorganic (mineral) filler and of at least one organic filler.

The filler may be chosen from pigments, titanium oxide, red iron oxide, yellow iron oxide, black iron oxide, boron nitride, nacres, synthetic or natural mica, nacres comprising mica and titanium oxide, silica powder, talc, polyamide particles and in particular those sold under the name Orgasol by the company Atochem, polyethylene powders, microspheres based on acrylic copolymers, such as those made of ethylene glycol dimethacrylate/lauryl methacrylate copolymer sold by the company Dow Corning under the name Polytrap, expanded powders such as hollow microspheres and in particular the microspheres sold under the name Expancel by the company Kemanord Plast or under the name Micropearl F 80 ED by the company Matsumoto, silicone resin microbeads such as those sold under the name Tospearl by the company Toshiba Silicone, and mixtures thereof.

These fillers may be present in amounts ranging from 0% to 20% by weight and preferably from 1% to 10% by weight relative to the total weight of the composition.

Preferably, the mass concentrations of filler range from 0.1% to 30% by weight and preferably from 0.5% to 15% by weight relative to the total weight of said composition.

Emulsifier

According to one embodiment, the composition according to the invention may also comprise at least one emulsifier.

When the composition according to the invention is a water-in-oil (W/O) or oil-in-water (O/W) emulsion, the proportion of the oily phase of the emulsion may range from 5% to 80% by weight, and preferably from 5% to 50% by weight, relative to the total weight of the composition.

The emulsions generally contain at least one emulsifier chosen from amphoteric, anionic, cationic and nonionic emulsifiers, used alone or as a mixture, and optionally a coemulsifier. The emulsifiers are chosen in an appropriate manner according to the emulsion to be obtained (W/O or O/W emulsion). The emulsifier and the coemulsifier are generally present in the composition in a proportion possibly ranging, for example, from 0.3% to 30% by weight and preferably from 0.5% to 20% by weight relative to the total weight of the composition.

For the W/O emulsions, examples of emulsifiers that may be mentioned include silicone emulsifiers such as dimethicone copolyols and ($C_8$-$C_{16}$)alkyldimethicone copolyols. One or more coemulsifiers may also be added thereto. The coemulsifier may be advantageously chosen from the group comprising polyol alkyl esters. Polyol alkyl esters that may notably be mentioned include glycerol and/or sorbitan esters, for example polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and any mixture thereof.

For the O/W emulsions, examples of emulsifiers that may be mentioned include nonionic surfactants, and notably esters of polyols and of fatty acids with a saturated or unsaturated chain including, for example, from 8 to 24 carbon atoms and better still from 12 to 22 carbon atoms, and the oxyalkylenated derivatives thereof, i.e. derivatives including oxyethylenated and/or oxypropylenated units, such as the glyceryl esters of $C_8$-$C_{24}$ fatty acids, and the oxyalkylenated derivatives thereof; the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; the sugar (sucrose, glucose or alkylglucose) esters of $C_8$-$C_{24}$ fatty acids, and the oxyalkylenated derivatives thereof; fatty alcohol ethers; the sugar ethers of $C_8$-$C_{24}$ fatty alcohols, and mixtures thereof.

According to a particular embodiment, the concentration of emulsifiers in the composition according to the invention ranges from 0.001% to 20% and preferably from 0.5% to 10% by weight relative to the total weight of the composition.

Thickener

Depending on the viscosity of the composition that it is desired to obtain, one or more thickeners and/or gelling agents, which are notably hydrophilic, that is to say water-soluble or water-dispersible, may be incorporated into the composition. Examples of hydrophilic gelling agents that may be mentioned include modified or unmodified carboxyvinyl polymers, such as the products sold under the names Carbopol (CTFA name: carbomer) and Pemulen (CTFA name: Acrylates/$C_{10-30}$ alkyl acrylate crosspolymer) by the company Goodrich; polyacrylamides; optionally crosslinked and/or neutralized 2-acrylamido-2-methylpropanesulfonic acid polymers and copolymers, for instance the poly(2-acrylamido-2-methylpropanesulfonic acid) sold by the company Hoechst under the name Hostacerin AMPS (CTFA name: Ammonium polyacryldimethyltauramide); crosslinked anionic copolymers of acrylamide and of AMPS, which are in the form of a W/O emulsion, such as those sold under the name Sepigel 305 (CTFA name: Polyacrylamide/$C_{13-14}$ Isoparaffin/Laureth-7) and under the name Simulgel 600 (CTFA name: Acrylamide/sodium acryloyldimethyltaurate copolymer/isohexadecane/polysorbate 80) by the company SEPPIC, polysaccharide biopolymers such as modified celluloses, carrageenans, in particular kappa-carrageenan, gellan gum, agar-agar, xanthan gum, alginate-based compounds, in particular sodium alginate, scleroglucan gum, guar gum, inulin and pullulan, cassia gum, karaya gum, konjac gum, gum tragacanth, tara gum, acacia gum or gum arabic, and mixtures thereof. The amount of gelling agents depends on the desired objective.

According to one embodiment, the amount of gelling agents ranges for example from 0.01% to 10%, for example from 0.1% to 5% by weight relative to the total weight of the composition.

Oily Phase

When the composition used according to the invention includes an oily phase, it preferably contains at least one oil, notably a cosmetic oil. It may also contain other fatty substances.

As oils that may be used in the composition of the invention, examples that may be mentioned include:

- hydrocarbon-based oils of animal origin, such as perhydrosqualene;
- hydrocarbon-based oils of plant origin, such as liquid fatty acid triglycerides including from 4 to 10 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarinerie Dubois or those sold under the names Miglyol 810, 812 and 818 by the company Dynamit Nobel, jojoba oil and shea butter oil;
- synthetic esters and ethers, notably of fatty acids, for instance the oils of formulae $R_1COOR_2$ and $R_1OR_2$ in which $R_1$ represents a fatty acid residue including from 8 to 29 carbon atoms and $R_2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate;
- hydroxylated esters, for instance isostearyl lactate, octyl hydroxystearate, octyldodecyl hydroxystearate, diisostearyl malate, triisocetyl citrate, and fatty alkyl heptanoates, octanoates and decanoates;
- polyol esters, for instance propylene glycol dioctanoate, neopentyl glycol diheptanoate and diethylene glycol diisononanoate;
- pentaerythritol esters, for instance pentaerythrityl tetraisostearate;
- linear or branched hydrocarbons of plant, mineral or synthetic origin, such as volatile or non-volatile liquid paraffins, and derivatives thereof, hydrocarbon-based oils bearing a branched chain including from 10 to 20 carbon atoms, such as isohexadecane, isododecane, isoparaffins and mixtures thereof, petroleum jelly, polydecenes, and hydrogenated polyisobutene such as Parleam Oil®;
- fatty alcohols and fatty acids containing from 8 to 26 carbon atoms, for instance cetyl alcohol or acid, stearyl alcohol, stearic acid, a mixture of cetyl alcohol and of stearyl alcohol (cetylstearyl alcohol), octyldodecanol, 2-butyloctanol, 2-hexyldecanol, 2-undecylpentadecanol, oleyl alcohol or linoleyl alcohol;
- partially hydrocarbon-based and/or silicone-based fluoro oils, such as those described in JP 2295912;
- silicone oils, for instance volatile or non-volatile polymethylsiloxanes (PDMS) with a linear or cyclic silicone chain, which are liquid or pasty at room temperature, notably cyclopolydimethylsiloxanes (cyclomethicones) such as cyclohexasiloxane; polydimethylsiloxanes including alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; and
- mixtures thereof.

In the list of oils mentioned above, the term "hydrocarbon-based oil" means any oil predominantly including carbon and hydrogen atoms, and possibly ester, ether, fluoro, carboxylic acid and/or alcohol groups.

The other fatty substances that may be present in the oily phase are, for example, fatty acids including from 8 to 30 carbon atoms, for instance stearic acid, lauric acid, palmitic acid and oleic acid; waxes, for instance lanolin wax, beeswax, carnauba wax or candelilla wax, paraffin wax, lignite wax or microcrystalline waxes, ceresin or ozokerite, and synthetic waxes, for instance polyethylene waxes and Fischer-Tropsch waxes; silicone resins such as trifluoromethyl-$C_1$-$C_4$-alkyl dimethicone and trifluoropropyl dimethicone; and silicone elastomers, for instance the products sold under the name KSG by the company Shin-Etsu, under the name Trefil or BY29 by the company Dow Corning, or under the name Gransil by the company Grant Industries.

These fatty substances may be chosen in a varied manner by a person skilled in the art in order to prepare a composition having the desired properties, for example in terms of consistency or texture.

Preferably, a composition according to the invention also comprises a fatty phase containing at least one fatty substance.

According to one variant, the amount of oily phase may range, for example, from 0.01% to 60%, for example from 5% to 50% by weight relative to the total weight of the composition.

According to one variant, the amount of oily phase may range, for example, from 10% to 40% by weight relative to the total weight of the composition.

Other Additives

The cosmetic composition may also include at least one additive chosen from the adjuvants typical of the cosmetic domain, such as hydrophilic or lipophilic gelling agents, water-soluble or liposoluble active agents, for example anti-ageing active agents, film-forming polymers, preserving agents, sequestrants, antioxidants, solvents, fragrances, odour absorbers, pH adjusters (acids or bases) and mixtures thereof.

According to a particular embodiment, the composition may comprise at least one hydrotropic molecule, for instance nicotinamide (vitamin B3), caffeine, sodium PCA, sodium salicylate, urea, hydroxyethyl urea, and any mixture thereof.

According to a particular embodiment of the invention, the composition may comprise at least one active agent. In particular, the active agent may be present in a composition according to the invention in a content of between 0.001% and 10% by weight and preferably between 0.01% and 5% by weight relative to the total weight of the composition.

According to one embodiment, the composition according to the invention may also comprise at least one preserving agent.

According to one embodiment, the composition also comprises a fragrance. According to one variant, the amount of fragrances may range, for example, from 0.001% to 10% and preferably from 0.01% to 5% by weight relative to the total weight of the composition.

A person skilled in the art will take care to select the optional additional adjuvants and/or the amount thereof so that the advantageous properties of the composition are not, or not substantially, adversely affected by the envisaged addition.

The compositions, notably the cosmetic compositions, according to the invention comprise a physiologically acceptable medium.

For the purposes of the present invention, the term "physiologically acceptable medium" is intended to denote a medium that is suitable for the topical administration of a composition.

A physiologically acceptable medium generally has no unpleasant odour or appearance, and is entirely compatible with topical administration. In the present case, where the composition is intended for topical administration, i.e. by application at the surface of the keratin material under consideration, such a medium is considered in particular to be physiologically acceptable when it does not cause stinging, tautness or redness that is unacceptable to the user.

In particular, the composition is suited to topical application, that is to say application on the surface of the skin, the scalp and/or the mucous membrane under consideration.

Thus, the physiologically acceptable medium is preferentially a cosmetically or dermatologically acceptable medium, i.e. a medium that has no unpleasant odour, colour or appearance, and that does not cause the user any unacceptable stinging, tautness or redness.

The composition may then comprise any constituent usually used in the envisaged application.

Needless to say, a person skilled in the art will take care to select this or these optional additional compound(s), and/or the amount thereof, such that the advantageous properties of the compounds according to the invention are not, or are not substantially, adversely affected by the envisaged addition.

A composition according to the invention is in particular a composition, notably a cosmetic composition, for making up and/or caring for keratin materials, preferably for caring for keratin materials, in particular the skin and/or the hair.

The compositions according to the invention may be in the form of products for caring for the skin or semi-mucous membranes, such as a protective or cosmetic care composition for the face, for the lips, for the hands, for the feet, for the anatomical folds or for the body (for example, day creams, night cream, day serum, night serum, makeup-removing cream, makeup base, antisun composition, protective or care body milk, aftersun milk, skincare or scalp-care lotion, gel or foam, serum, mask, or aftershave composition).

The compositions according to the invention may also be in the form of products for caring for keratin fibres, in particular the hair.

Preferably, a composition according to the invention is a composition for caring for keratin materials, preferably for caring for the skin.

According to a preferred embodiment, a composition according to the invention is a composition for caring for keratin fibres, preferably for haircare.

Specifically, a composition according to the invention also makes it possible to give the hair good body and volume, in particular for fine hair, to maintain the curls, or to slow down the re-greasing of the hair.

Thus, a subject of the present invention is also a process for washing or conditioning keratin materials such as the hair, which consists in applying to said wet materials an effective amount of a composition as defined above, and then in optionally rinsing with water after an optional leave-in time.

For the purposes of the present invention, the term "keratin material" is intended to cover the skin, mucous membranes such as the lips, the nails and keratin fibres, such as the eyelashes and the hair. The skin and/or the hair are most particularly considered according to the invention.

The term "skin" means all of the skin of the body, including the scalp, the mucous membranes, the semi-mucous membranes, and the skin integuments. The term "skin integuments" means bodily hair, the eyelashes, head hair and the nails. More particularly, in the present invention, the skin of the neckline, of the neck and of the face, and notably the skin of the face, are considered.

A composition according to the invention preferably has a viscosity of between 0.1 Pa·s and 2000 Pa·s, better still between 1 Pa·s and 1000 Pa·s, and even better still between 10 Pa·s and 500 Pa·s.

The viscosity of the composition is measured at room temperature (25° C.) using a Haake MARS (Modular Advanced Rheometer System) rheometer equipped with a rotor to which the geometries are attached. In the context of the present invention, the cone/plate geometry was used.

A composition according to the invention is of gel type, in particular of aqueous gel type.

Preferably, it is an emulsion, notably a water-in-oil or oil-in-water emulsion, and preferably an oil-in-water emulsion.

Advantageously, the pH of the composition is between 4 and 8 and preferably between 5 and 7.

Throughout the description, including the claims, the term "including a" should be understood as being synonymous with "including at least one", unless otherwise specified.

The expressions "between . . . and . . . ", and "ranging from . . . to . . . " should be understood as meaning limits included, unless otherwise specified.

In the description and the examples, the percentages are weight percentages, unless otherwise indicated. The percentages are thus expressed on a weight basis relative to the total weight of the composition. The temperature is expressed in degrees Celsius, unless otherwise indicated, and the pressure is atmospheric pressure, unless otherwise indicated.

The invention is illustrated in greater detail by the non-limiting examples presented below.

EXAMPLES

Example 1: Compositions 1 to 7

Seven hectorite-based gel-type compositions were prepared from the compounds and contents detailed in Table 1 below. The contents are expressed as weight percentages relative to the total weight of the composition.

TABLE 1

| Compounds | Formulation 1 | Formulation 2 according to the invention | Formulation 3 according to the invention | Formulation 4 | Formulation 5 | Formulation 6 | Formulation 7 |
|---|---|---|---|---|---|---|---|
| Hectorite (INCI name: Hectorite) Bentone EW from Elementis Specialties | 5 | 5 | 5 | 5 | 5 | 5 | 5 |
| Pectin (INCI name: Pectin and Sucrose) Unipectine Of 600 C SB from Cargill France | / | 0.25 (*0.2) | 0.63 (*0.5) | / | / | / | / |
| Xanthan gum Rhodicare CFT from Rhodia (Solvay) | / | / | / | 0.2 | 0.5 | / | / |
| Scleroglucan gum Amigum from Alban Muller | / | / | / | / | / | 0.2 | 0.5 |
| Caprylyl glycol | 0.5 | 0.5 | 0.5 | 0.5 | 0.5 | 0.5 | 0.5 |
| Water | qs 100 | qs 100 | qs 100 | qs 100 | qs 100 | qs 100 | qs 100 |
| pH | 9.6 | 8.2 | 7.5 | 9.3 | 9.2 | 9.3 | 9.5 |

*% of active material

The compositions are prepared according to the protocol indicated below:

- the hectorite is introduced into the water with vigorous stiffing at a temperature of 80° C.;
- where appropriate, the pectin or the xanthan gum or the scleroglucan gum is introduced into the preceding mixture with stirring; and
- the caprylyl glycol is added.

Compositions 1 (hectorite alone) and 4 to 6 (comprising xanthan gum or scleroglucan gum) have a high pH. Only the combination of hectorite and pectin makes it possible to lower the pH of the compositions (compositions 2 and 3 according to the invention).

Example 2: Comparative Compositions 8 to 14

Seven bentonite-based gel-type compositions were prepared from the compounds and contents detailed in Table 2 below. The contents are expressed as weight percentages relative to the total weight of the composition.

TABLE 2

| Compounds | Formulation 8 | Formulation 9 | Formulation 10 | Formulation 11 | Formulation 12 | Formulation 13 | Formulation 14 |
|---|---|---|---|---|---|---|---|
| Bentonite Optigel CK-BYK from Additives & Instruments | 5 | 5 | 5 | 5 | 5 | 5 | 5 |
| Pectin (INCI name: Pectin and Sucrose) Unipectine Of 600 C SB from Cargill France | / | 0.25 (*0.2) | 0.63 (*0.5) | / | / | / | / |
| Xanthan gum Rhodicare CFT from Rhodia (Solvay) | / | / | / | 0.2 | 0.5 | / | / |
| Scleroglucan gum Amigum from Alban Muller | / | / | / | / | / | 0.2 | 0.5 |
| Caprylyl glycol | 0.5 | 0.5 | 0.5 | 0.5 | 0.5 | 0.5 | 0.5 |
| Water | qs 100 | qs 100 | qs 100 | qs 100 | qs 100 | qs 100 | qs 100 |
| pH | 10.5 | 10.3 | 9.9 | 10.4 | 10.3 | 10.5 | 10.5 |

*% of active material

The compositions are prepared according to the protocol indicated below:

- the bentonite is introduced into the water with vigorous stirring at 80° C.;
- where appropriate, the pectin or the xanthan gum or the scleroglucan gum is introduced into the preceding mixture with stirring; and
- the caprylyl glycol is added.

Irrespective of the type of polymer used in combination with the bentonite, the pH of the comparative compositions 8 to 14 remains high. Furthermore, compositions 8 to 10 and 13 are unstable.

Example 3: Comparative Compositions 15 to 21

Seven montmorillonite-based compositions were prepared from the compounds and contents detailed in Table 3 below. The contents are expressed as weight percentages relative to the total weight of the composition.

TABLE 3

| Compounds | Formulation 15 | Formulation 16 | Formulation 17 | Formulation 18 | Formulation 19 | Formulation 20 | Formulation 21 |
|---|---|---|---|---|---|---|---|
| Montmorillonite Gel White-H XR BYK from Additives & Instruments | 5 | 5 | 5 | 5 | 5 | 5 | 5 |
| Pectin (INCI name: Pectin and Sucrose) Unipectine Of 600 C SB from Cargill France | / | 0.25 (*0.2) | 0.63 (*0.5) | / | / | / | / |
| Xanthan gum Rhodicare CFT from Rhodia (Solvay) | / | / | / | 0.2 | 0.5 | / | / |
| Scleroglucan gum Amigum from Alban Muller | / | / | / | / | / | 0.2 | 0.5 |
| Caprylyl glycol | 0.5 | 0.5 | 0.5 | 0.5 | 0.5 | 0.5 | 0.5 |
| Water | qs 100 | qs 100 | qs 100 | qs 100 | qs 100 | qs 100 | qs 100 |
| pH | 9.4 | 8.5 | 7.7 | 9.3 | 9.2 | 9.4 | 8 |

*% of active material

The compositions are prepared according to the protocol indicated below:

the montmorillonite is introduced into the water with vigorous stiffing at 80° C.;

where appropriate, the pectin or the xanthan gum or the scleroglucan gum is introduced into the preceding mixture with stirring; and the caprylyl glycol is added.

Compositions 15 to 18 and 21 are liquid and not of gel type. Furthermore, the pH of compositions 15, 16 and 18 to 20 remains high.

Example 4: Comparative Compositions 22 to 28

Seven compositions based on purified smectite were prepared from the compounds and contents detailed in Table 4 below. The contents are expressed as weight percentages relative to the total weight of the composition.

TABLE 4

| Compounds | Formulation 22 | Formulation 23 | Formulation 24 | Formulation 25 | Formulation 26 | Formulation 27 | Formulation 28 |
|---|---|---|---|---|---|---|---|
| Purified smectite Veegum from Vanderbilt | 5 | 5 | 5 | 5 | 5 | 5 | 5 |
| Pectin (INCI name: Pectin and Sucrose) Unipectine Of 600 C SB from Cargill France | / | 0.25 (*0.2) | 0.63 (*0.5) | / | / | / | / |
| Xanthan gum Rhodicare CFT from Rhodia (Solvay) | / | / | / | 0.2 | 0.5 | / | / |
| Scleroglucan gum Amigum from Alban Muller | / | / | / | / | / | 0.2 | 0.5 |
| Caprylyl glycol | 0.5 | 0.5 | 0.5 | 0.5 | 0.5 | 0.5 | 0.5 |
| Water | qs 100 | qs 100 | qs 100 | qs 100 | qs 100 | qs 100 | qs 100 |
| pH | 9.4 | 8.1 | 8 | 9.3 | 9.2 | 9.4 | 9.4 |

*% of active material

The compositions are prepared according to the protocol indicated below:

the purified smectite is introduced into the water with vigorous stirring at 80° C.;

where appropriate, the pectin or the xanthan gum or the scleroglucan gum is introduced into the preceding mixture with stirring; and the caprylyl glycol is added.

Compositions 22 to 25 and 27 are liquid and not of gel type. Furthermore, the pH of compositions 22 and 25 to 28 remains high.

Example 5: Comparative Compositions 29 to 35

Seven kaolin-based compositions were prepared from the compounds and contents detailed in Table 5 below. The contents are expressed as weight percentages relative to the total weight of the composition.

TABLE 5

| Compounds | Formulation 29 | Formulation 30 | Formulation 31 | Formulation 32 | Formulation 33 | Formulation 34 | Formulation 35 |
|---|---|---|---|---|---|---|---|
| Kaolin Imercare 04K from Imerys | 5 | 5 | 5 | 5 | 5 | 5 | 5 |
| Pectin (INCI name: Pectin and Sucrose) Unipectine Of 600 C SB from Cargill France | / | 0.25 (*0.2) | 0.63 (*0.5) | / | / | / | / |
| Xanthan gum Rhodicare CFT from Rhodia (Solvay) | / | / | / | 0.2 | 0.5 | / | / |
| Scleroglucan gum Amigum from Alban Muller | / | / | / | / | / | 0.2 | 0.5 |
| Caprylyl glycol | 0.5 | 0.5 | 0.5 | 0.5 | 0.5 | 0.5 | 0.5 |
| Water | qs 100 | qs 100 | qs 100 | qs 100 | qs 100 | qs 100 | qs 100 |
| pH | 5.5 | 5.4 | 5.4 | 5.5 | 5.4 | 5.5 | 5.6 |

*% of active material

The compositions are prepared according to the protocol indicated below:

the kaolin is introduced into the water with vigorous stiffing at a temperature of 80° C.;

where appropriate, the pectin or the xanthan gum or the scleroglucan gum is introduced into the preceding mixture with stirring; and the caprylyl glycol is added.

None of the compositions 29 to 35 comprising kaolin makes it possible to form a gel, the compositions are liquid. In addition, compositions 29 to 31, 34 and 35 are neither homogeneous nor stable, the kaolin sediments out.

Example 6: Compositions 36 and 37 According to the Invention

Face mask compositions were prepared from the compounds and contents detailed in Table 6 below. The contents are expressed as weight percentages relative to the total weight of the composition. The compositions were formulated at a pH equal to 5.

TABLE 6

| Compounds | | Formulation 36 | Formulation 37 |
|---|---|---|---|
| Sodium Hyaluronate Cristalhyal LO Soliance from Givaudan | A3 | 0.05 | 0.05 |
| Sucrose Sucre Cristal Numéro 1 Pure Canne 1500 from Tereos | A4 | 5.5 | 5.5 |
| Hectorite (INCI name: Hectorite) Bentone EW from Elementis Specialties | A2 | 3 | 3 |
| Phenoxyethanol (and) Methylparaben (and) Ethylparaben (and) Propylparaben (and) Isobutylparaben (and) Butylparaben Phenonip from Clariant | A5 | 0.5 | 0.5 |
| Sodium Phytate Dermofeel PA-3 from Dr Straetmans | A6 | 0.15 | 0.15 |
| Pectin (INCI name: Pectin and Sucrose) Unipectine Of 600 C SB from Cargill France | B1 | 2 (*1.6) | 2 (*1.6) |
| Glycerin | B2 | / | 16 |
| Propanediol | A7 | / | 5 |
| Cocoyl Betaine Tego Betain AB 1214 from Evonik Goldschmidt | C | 0.5 | 0.5 |
| Water | A1 | qs 100 | qs 100 |

*% of active material

The compositions are prepared according to the protocol indicated below:

A2 is introduced into A1 with vigorous stirring at a temperature of 80° C.;

A3 and A4 are introduced into the mixture with stiffing;

A5, A6 and A7 are then added with stiffing;

B1 and B2 are mixed, and the mixture is introduced into the preceding phase;

C is added with stiffing.

The compositions are stable and homogeneous.

In Vitro Gloss Measurement

Gloss measurements were taken on these compositions, in order to evaluate the matt effect.

The gloss measurements are expressed in GU (gloss units). They are taken on films of 100 μm of composition formed on contrast cards and measured using a 60° microgloss glossmeter from Byk Gardner. The calculations are performed by difference relative to a positive control and a negative control. The performance at the various times is calculated via the relationship:

$$\text{Performance index } (fle\ n°, t) = \frac{GU\ (fle\ n°, t) - GU\ (fle \text{ negative control}, t)}{GU\ (fle \text{ positive control}, t) - GU\ (fle \text{ negative control}, t)}$$

The negative control is a cream gel free of fillers, the gloss measurement of which is about 70 GU and the performance index of which is 0 (very glossy formulation). The positive control is a cream gel comprising 2% by weight of Aerogel, the gloss measurement of which is about 2-3 GU and the performance index of which is 100% at t=0 minutes, and is stable over time (very matt formulation).

The gloss measurements are taken at t=0, 6, 12 and 18 minutes.

The results are reported in Table 7 below.

TABLE 7

| Measurements and performances | Formulation 36 | Formulation 37 |
|---|---|---|
| Measurement at t = 0 minutes (GU) | 9.2 +/− 0.8 | 7.2 +/− 0.2 |
| Measurement at t = 6 minutes (GU) | 11.4 +/− 2.6 | 8.3 +/− 0.1 |
| Measurement at t = 12 minutes (GU) | 9.8 +/− 0.9 | 9.5 +/− 0.5 |
| Measurement at t = 18 minutes (GU) | 17.8 +/− 2.7 | 10.8 +/− 1.2 |
| Performance (%) at t = 0 minutes | 90.2 | 93.1 |
| Performance (%) at t = 6 minutes | 74.1 +/− 0.5 | 83.1 +/− 0.5 |
| Performance (%) at t = 12 minutes | 77.7 +/− 0.36 | 78.7 +/− 0.34 |
| Performance (%) at t = 18 minutes | 68.1 +/− 0.53 | 74.1 +/− 0.63 |

The results show that compositions 36 and 37 according to the invention are matt and that their performance qualities remain stable over time.

Example 7: Composition 38 According to the Invention

A base which is useful for the manufacture of a clay-based DIY (do-it-yourself) mask was prepared from the compounds and contents detailed in Table 8 below. The contents are expressed as weight percentages relative to the total weight of the composition.

TABLE 8

| Compounds | Formulation 38 |
|---|---|
| Pectin (INCI name: Pectin and Sucrose) Unipectine Of 600 C SB from Cargill France | 1 (*0.8) |
| Waxy maize starch C* Gel 04201 from Cargill | 89 |
| Hectorite (INCI name: Hectorite) Bentone EW from Elementis Specialties | 10 |

*% of active material

This base is to be mixed with warm or hot water in order to make a gel or a paste. The preparation thus obtained is to be applied to the face as a mask.

Advantageously, the base does not contain any preserving agents. The active agents may be added by the consumer in order to personalize his or her care. In addition, the consumer can choose himself or herself the consistency of his or her preparation.

The preparation applied as a thick coat as a care mask can be left on the skin until dry and is then removed with water or a wet glove, or else it can be applied via a particular action directed rather towards cleansing.

After removing the composition, the skin is soft and does not shine.

Example 8: Composition 39 According to the Invention

A matt-effect care cream composition was prepared from the compounds and contents detailed in Table 9 below. The contents are expressed as weight percentages relative to the total weight of the composition.

TABLE 9

| Phase | Compounds | Formulation 39 |
|---|---|---|
| A1 | Microbiologically clean deionized water | 57 |
| A2 | Hectorite (INCI name: Hectorite) Bentone EW from Elementis Specialties | 3 |
| A3 | Phytic acid (and) water Phytic acid 50% solution from Tsuto Rice Fine Chemicals | 0.15 |
| A4 | Pectin (INCI name: Pectin and Sucrose) Unipectine Of 600 C SB from Cargill France | 1 (*0.8) |
| B1 | Cetylstearyl alcohol (50/50 $C_{16}/C_{18}$) Lanette O OR from BASF | 3 |
| B1 | Mixture of myristyl stearate and myristyl palmitate Crodamol MS-PA-(MH) from Croda | 0.5 |
| B1 | Fatty acids (predominantly stearic acid) Palmera B1802CG from KLK Oleo | 0.2 |
| B1 | Apricot kernel oil Apricot kernel oil refined from Naturex | 1.5 |
| B2 | Mixture of natural alpha, beta, gamma and delta tocopherols in sunflower oil (90/10) COVI-OX T 90 EU C from BASF | 0.2 |
| C | Microbiologically clean deionized water | qs 100 |
| C | Glycerol | 7 |
| D | Propane-1,3-diol | 4 |
| E | Octane-1,2-diol | 0.5 |

*% of active material

The composition is prepared according to the protocol indicated below:

- A2 is introduced into A1 with vigorous stirring at a temperature of 80° C.;
- A3 and then A4 are introduced into the mixture with stiffing;
- the oily phase B1 is prepared at 70° C., and B2 is then added thereto;
- the mixture B1 and B2 is added to the aqueous phase;
- the mixture is emulsified and then cooled;
- C, D and E are added with stirring.

The composition obtained is in the form of a cream.

Advantageously, the composition is fresh, light, non-tacky and non-runny on application. It spreads easily without soaping and its pH is close to that of the skin. After application to the face and drying, a long-lasting matt effect is observed.

Example 9: Composition 40 According to the Invention

A volumizing shampoo composition was prepared from the compounds and contents detailed in Table 10 below. The contents are expressed as weight percentages relative to the total weight of the composition.

TABLE 10

| Phase | Compounds | Formula 40 |
|---|---|---|
| A2 | Hectorite (INCI name: Hectorite) Bentone EW from Elementis Specialties | 2 |
| A3 | Pectin (INCI name: Pectin and Sucrose) Unipectine Of 600 C SB from Cargill France | 1.5 (*1.2) |
| B1 | Sodium lauroyl Sarcosinate as an aqueous 30% solution Oramix L 30 from SEPPIC | *6 |
| B2 | (50/50 $C_8/C_{10}$)alkyl polyglucoside (2) as an aqueous 60% solution Oramix CG 110 from SEPPIC | *4 |
| B3 | ($C_8/C_{16}$)alkyl polyglucoside (1.4) as an aqueous 53% solution Plantacare 818 UP from BASF | 5 |
| C | Refined soybean oil Refined CT soybean oil from Zor | 1 |
| D1 | Salicylic acid Salicylic acid USP from Alta Laboratories | 0.3 |
| D2 | Citric acid monohydrate | 1 |
| D3 | Sodium benzoate | 0.5 |
| D4 | Octane-1,2-diol | 1 |
| A1 | Microbiologically clean deionized water | qs 100 |

*% of active material

The composition is prepared according to the protocol indicated below:

- A2 and then A3 are introduced into A1 with vigorous stiffing at a temperature of 80° C.;
- B1, then B2 and then B3 are introduced into the mixture with stirring;
- C is introduced with stirring;
- D1, then D2, then D3 and then D4 are introduced into the mixture.

Advantageously, the shampoo according to the invention spreads and foams easily. The foam is abundant and creamy. The composition is easy to rinse out and the hair is clean after rinsing.

After drying, the hair is easy to style and has more volume than in the case of washing with conventional shampoos.

Example 10: Composition 41 According to the Invention

A composition according to the invention was prepared from the compounds and contents detailed in Table 11 below. The contents are expressed as weight percentages relative to the total weight of the composition.

TABLE 11

| Compounds | Formulation 41 according to the invention |
|---|---|
| L-arginine | 0.2 |
| Hectorite (INCI name: Hectorite) Bentone EW from Elementis Specialties | 1 |
| Preserving agent | 0.5 |
| Pectin (INCI name: Pectin and Sucrose) Unipectine Of 600 C SB from Cargill France | 2 (*1.6) |
| Water | qs 100 |

*% of active material

The composition is prepared according to the protocol indicated below:

- the hectorite is introduced into the water with vigorous stiffing at a temperature of 80° C.;
- the pectin and the L-arginine are introduced into the preceding mixture with stirring; and
- the preserving agent is added.

Matt-Effect Performance

In order to demonstrate the persistence of the matt effect over time, the matt effect of the composition was evaluated in vivo, at t=0 minutes and two hours after application. To do this, the composition is applied to the face of users and measurements of the matt effect are taken at t=0 minutes and at t=10 minutes. The users then stay for 2 hours in a steam room and new measurements are taken.

The results show that composition 41 according to the invention is matt. Furthermore, it affords greater persistence of the matt effect after 2 hours.

Antipollution Performance

The composition was subjected to an in vitro antipollution test.

The antipollution performance is evaluated via in vitro evaluation of the anti-adhesion capacity by following a protocol which uses activated charcoal particles as pollutant and image analysis for quantification of the adhesion of particles.

The formulation is applied to the support known as BioSkin, the size of which is 5 cm×5 cm. After 20 minutes, about 8 g of activated charcoal are deposited. Photographs are taken and image analysis is performed after the deposition of the activated charcoal particles and after blowing with air in order to determine the area covered by said particles.

The performance is then expressed via the percentage of activated charcoal particles which have been able to be removed by blowing with air.

The results show that composition 41 according to the invention is efficient.

Example 11: Compositions 42 to 46

Five compositions according to the invention and outside the invention were prepared from the compounds and contents detailed in Table 12 below. The contents are expressed as weight percentages relative to the total weight of the composition.

TABLE 12

| Compounds | Phase | Formulation 42 according to the invention | Formulation 43 according to the invention | Formulation 44 according to the invention | Formulation 45 according to the invention | Formulation 46 outside the invention |
|---|---|---|---|---|---|---|
| Hectorite (INCI name: Hectorite) Bentone EW from Elementis Specialties | A2 | 3 | 3 | 3 | 5 | / |
| Montmorillonite Gel White-H XR BYK from Additives & Instruments | A2' | / | / | / | / | 3 |
| Phenoxyethanol | A4 | 0.5 | 0.5 | 0.5 | 0.5 | 0.5 |
| Pectin (INCI name: Pectin and Sucrose) Unipectine Of 600 C SB from Cargill France | A3 | 2 (*1.6) | 1 (*0.8) | 0.5 (*0.4) | 2 (*1.6) | 2 (*1.6) |
| Water | A1 | qs 100 | qs 100 | qs 100 | qs 100 | qs 100 |
| pH | | 5.2 | 5.2 | 5.2 | 5.2 | 5.2 |

*% of active material

The compositions are prepared according to the protocol indicated below:

A2 (or A2') is introduced into A1 with vigorous stiffing at a temperature of 80° C.;

A3 and A4 are introduced into the mixture with stiffing.

The compositions are stable.

The films formed from compositions 42 to 45 according to the invention are homogeneous and matt. In contrast, the films formed from composition 46 outside the invention with montmorillonite are not homogeneous and do not make it possible to take gloss measurements.

Gloss measurements were taken on compositions 42 to 45 according to the protocol detailed in Example 6, in order to evaluate the matt effect.

The results are detailed in Table 13 below.

TABLE 13

| Measurements and performance | Formulation 42 according to the invention | Formulation 43 according to the invention | Formulation 44 according to the invention | Formulation 45 according to the invention |
|---|---|---|---|---|
| Measurement at t = 0 minutes (GU) | 19.4 +/− 0.2 | 14.8 +/− 0.4 | 15.9 +/− 0.5 | 12.7 +/− 0.1 |
| Measurement at t = 6 minutes (GU) | 15.0 +/− 0.5 | 11 +/− 2.8 | 14.2 +/− 0.7 | 14.8 +/−3.1 |
| Measurement at t = 12 minutes (GU) | 16.4 +/− 3 | 17.5 +/− 5.6 | 17.6 +/− 1.6 | 13.7 +/−5.5 |
| Measurement at t = 18 minutes (GU) | 19 +/− 1.7 | 15.7 +/− 0.3 | 17.1 +/− 1.5 | 17.2 +/−5.8 |
| Performance (%) at t = 0 minutes | 50 +/− 0.27 | 63.9 +/− 0.32 | 60.5 +/− 0.32 | 70.2 +/− 0.33 |
| Performance (%) at t = 6 minutes | 66.2 +/− 0.71 | 77.7 +/− 0.89 | 68.5 +/− 0.74 | 66.8 +/− 0.79 |
| Performance (%) at t = 18 minutes | 64.4 +/− 0.11 | 81.7 +/− 0.03 | 74.3 +/− 0.1 | 73.8 +/− 0.32 |

The results show that compositions 42 to 45 according to the invention are matt and that their performance qualities remain stable over time.

Example 12: Compositions 47 to 51

Five compositions according to the invention and outside the invention were prepared from the compounds and contents detailed in Table 14 below. The contents are expressed as weight percentages relative to the total weight of the composition.

TABLE 14

| Compounds | Phase | Formulation 47 according to the invention | Formulation 48 according to the invention | Formulation 49 outside the invention | Formulation 50 outside the invention | Formulation 51 outside the invention |
|---|---|---|---|---|---|---|
| Hectorite (INCI name: Hectorite) Bentone EW from Elementis Specialties | A2 | 3 | 3 | 3 | 3 | 3 |
| Cocoyl Betaine Tego Betain AB 1214 from Evonik Goldschmidt | B | / | 0.5 | / | / | 0.5 |
| Pectin (INCI name: Pectin and Sucrose) Unipectine Of 600 C SB from Cargill France | A3 | 2 (*1.6) | 2 (*1.6) | / | / | / |
| Water | A1 | qs 100 | qs 100 | qs 100 | qs 100 | qs 100 |
| pH | | 5 | 5 | 5 | 8 | 5 |

*% of active material

The compositions are prepared according to the protocol indicated below:

A2 is introduced into A1 with vigorous stirring at a temperature of 80° C.;

A3 is introduced into the mixture; and

B is introduced into the mixture.

Compositions 47 and 48 according to the invention are stable. Comparative compositions 49 to 51 are unstable. The films formed from composition 51 outside the invention are not homogeneous. Comparative compositions 49 and 51 do not make it possible to take gloss measurements.

The films formed from compositions 47, 48 and 50 are homogeneous and matt. Gloss measurements were taken on these compositions according to the protocol detailed in Example 6, in order to evaluate the matt effect.

The results are detailed in Table 15 below.

TABLE 15

| Measurements and performance | Formulation 47 according to the invention | Formulation 48 according to the invention | Formulation 50 outside the invention |
|---|---|---|---|
| Measurement at t = 0 minutes (GU) | 14 +/− 0.2 | 9 +/− 0.2 | 8 +/− 0.8 |
| Measurement at t = 6 minutes (GU) | 12 +/− 0.2 | 9.1 +/− 0.6 | 28 +/− 3.9 |
| Measurement at t = 12 minutes (GU) | 11.5 +/− 0.6 | 11.5 +/−3.6 | 53 +/− 8.4 |
| Measurement at t = 18 minutes (GU) | 9.7 +/− 0.5 | 12.1 +/− 2.7 | 72.2 +/− 5.8 |
| Performance (%) at t = 0 minutes | 79 | 88.3 | 92 |
| Performance (%) at t = 6 minutes | 78.1 +/− 2.52 | 85.6 +/− 2.75 | 40.7 +/− 0.35 |
| Performance (%) at t = 12 minutes | 75.9 +/− 0.03 | 75.9 +/− 0.15 | −41.8 +/− 0.35 |
| Performance (%) at t = 18 minutes | 68.3 +/− 0.94 | 55.2 +/− 0.95 | −136.6 +/− 1.85 |

The results show that compositions 47 and 48 according to the invention are matt and that their performance qualities remain stable over time. In contrast, the performance qualities over time of composition 50 outside the invention decrease greatly; the composition does not stay matt.

The invention claimed is:

1. A composition, comprising:

water;

at least one pectin; and at least one unmodified hectorite, wherein the composition is an aqueous gel having a viscosity from 1 Pa·s to 2000 Pa·s, a content of water is from 67.3% to 95.4% by weight relative to the total weight of the composition, a content of the at least one pectin is from 0.1% to 2% by weight relative to the total weight of the composition, and a content of the at least one unmodified hectorite is from 2% to 10% by weight relative to the total weight of the composition.

2. The composition according to claim 1, wherein the at least one unmodified hectorite is present in a content of from 2% to 5% by weight, relative to the total weight of the composition.

3. The composition according to claim 1, wherein the at least one pectin is selected from the group consisting of non-methoxy pectins and low-methoxy pectins.

4. The composition according to claim 1, wherein the at least one pectin is present in a content of from 0.5% to 2.0% by weight of active material, relative to the total weight of the composition.

5. The composition according to claim 1, wherein the unmodified hectorite/pectin mass ratio is between 10/1 and 1/1.

6. The composition according to claim 1, further comprising sucrose.

7. The composition according to claim 1, further comprising a surfactant wherein the surfactant is a betaine.

8. The composition according to claim 7, wherein the surfactant is present in a content of between 0.15% and 5% by weight of active material relative to the total weight of the composition.

9. The composition according to claim 1, further comprising at least one alcohol.

10. The composition according to claim 1, wherein the composition is suitable for making up and/or caring for keratin materials.

11. The composition according to claim 1, wherein the composition is suitable as a skincare composition.

12. The composition according to claim 1 wherein the composition is suitable as a haircare composition.

13. The composition according to claim 1 wherein the composition is suitable as a cosmetic composition.

14. The composition according to claim 1 wherein the at least one pectin is selected from the group consisting of non-methoxy pectins and pectins comprising a degree of methoxylation of less than 50%.

15. The composition according to claim 7, wherein the surfactant is cocoyl betaine or cocamidopropyl betaine.

16. The composition according to claim 1 further comprising at least one glycol.

17. The composition according to claim 1, wherein the viscosity is between 1 Pa·s and 500 Pa·s.

18. A cosmetic process, comprising: applying to the skin and/or the hair a gel composition comprising the composition according to claim 1.

* * * * *